United States Patent
Graßl et al.

(10) Patent No.: US 10,959,623 B2
(45) Date of Patent: Mar. 30, 2021

(54) BLOOD PRESSURE CUFF

(71) Applicant: Drägerwerk AG & Co. KGaA, Lübeck (DE)

(72) Inventors: Thomas Graßl, Lübeck (DE); Alexander Horn, Tettnang (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 774 days.

(21) Appl. No.: 15/254,224

(22) Filed: Sep. 1, 2016

(65) Prior Publication Data

US 2017/0055857 A1   Mar. 2, 2017

(30) Foreign Application Priority Data

Sep. 2, 2015 (DE) ..................... 10 2015 011 298.8

(51) Int. Cl.
*A61B 5/022* (2006.01)
(52) U.S. Cl.
CPC .... *A61B 5/02241* (2013.01); *A61B 2503/045* (2013.01); *A61B 2562/12* (2013.01)
(58) Field of Classification Search
CPC .......... A61B 2503/045; A61B 5/02241; A61B 5/02233; A61B 17/135; A61B 5/02141
See application file for complete search history.

(56) References Cited

U.S. PATENT DOCUMENTS

| | | | | |
|---|---|---|---|---|
| 2,569,643 A | * | 10/1951 | Spare | ........................ A41B 1/00 2/115 |
| 5,193,549 A | * | 3/1993 | Bellin | ................ A61B 5/02233 128/DIG. 20 |
| 2004/0095648 A1 | * | 5/2004 | McCannel | .............. B29C 49/20 359/619 |
| 2006/0027946 A1 | * | 2/2006 | Kawamura | ........ A61B 5/02233 264/239 |

FOREIGN PATENT DOCUMENTS

| | | |
|---|---|---|
| EP | 1 623 815 A1 | 2/2006 |
| WO | 2012/078235 A1 | 6/2012 |

* cited by examiner

*Primary Examiner* — Etsub D Berhanu
*Assistant Examiner* — Michael A Catina
(74) *Attorney, Agent, or Firm* — McGlew and Tuttle, P.C.

(57) ABSTRACT

A blood pressure cuff (10), for determining the blood pressure in newborns, includes a chamber section (20) with an air chamber (22) and a handling section (30) for placing and fastening the chamber section (20) around an arm (100) of a newborn. The air chamber (22) has a chamber wall (24), which has, along a circumferential direction (U) of the air chamber (22), a longitudinal sealing seam (40). Two longitudinal edges (26a, 26b) of the chamber wall (24) are connected to one another overlappingly opposite each other in an airtight manner by the longitudinal sealing seam (40).

20 Claims, 3 Drawing Sheets

BLOOD PRESSURE CUFF

CROSS REFERENCE TO RELATED APPLICATIONS

This application claims the benefit of priority under 35 U.S.C. § 119 of German Application 10 2015 011 298.8 filed Sep. 2, 2015, the entire contents of which are incorporated herein by reference.

FIELD OF THE INVENTION

The present invention pertains to a blood pressure cuff for determining the blood pressure of newborns as well as to a method for manufacturing such a blood pressure cuff.

BACKGROUND OF THE INVENTION

It is known, in principle, that the blood pressure is measured in persons by means of so-called blood pressure cuffs. For such a measurement, the blood pressure cuffs have an air chamber, which is placed around the arm of the person in question. The air chamber is subsequently filled with air, so that a radially inwardly acting compressive force is applied by the overpressure to the patient's arm. The upper value and the lower value of the blood pressure can be determined by specifically releasing air and monitoring the pulse in the area of the blood pressure cuff.

Blood pressure cuffs are also used for newborns. Neonates, children who are born in the hospital are also called newborns. This term pertains in the sense of the present invention to both premature babies and full-term or post-term babies. The prior-art blood pressure cuffs have the drawback that they may exert a relatively great adverse mechanical effect on the child's arm. This can be attributed, in particular, to the circumstance that the prior-art blood pressure cuffs have two-layer chamber walls, which are welded together along the circumference of a corresponding chamber section. Similarly to an arm float for children, sharp-edged sealing seams are formed, which may lead to an undesired adverse effect on the skin and tissue especially if the blood pressure cuff slips in the bend of the elbow or in the armpit. It should be borne in mind, in particular, that such blood pressure cuffs may be placed on newborns not only for a short time but also over a longer time, at times even over several weeks.

SUMMARY OF THE INVENTION

An object of the present invention is to at least partially eliminate the above-described drawbacks. In particular, an object of the present invention is to improve the wearing comfort of a blood pressure cuff for newborns in a cost-effective and simple manner.

The above object is accomplished by a blood pressure cuff for determining blood pressure in newborns. The blood pressure cuff has a chamber section with an air chamber and a handling section for placing and fastening the chamber section around the arm of a patient, especially a newborn. The air chamber has a chamber wall, which has, along a circumferential direction of the air chamber, a longitudinal sealing seam, by means of which two longitudinal edges of the chamber wall are connected to one another overlappingly opposite each other in an airtight manner. Features and details that are described in connection with the blood pressure cuff according to the present invention also apply, of course, in connection with the method according to the present invention and also vice versa, so that reference is and can always mutually be made to the individual aspects of the present invention concerning the disclosure.

A blood pressure cuff according to the present invention is used to determine the blood pressure in newborns. For this, the blood pressure cuff has a chamber section with an air chamber and a handling section for placing and fastening the chamber section around an arm of a newborn. A blood pressure cuff according to the present invention is characterized in that the air chamber has a chamber wall, which has a longitudinal sealing seam along a circumferential direction of the air chamber. Two longitudinal edges of the chamber wall are connected by means of this longitudinal sealing seam opposite and overlapping each other in an airtight manner.

Consequently, according to the present invention the airtight closure of the air chamber is perfected. This air chamber is provided according to the invention with a longitudinal sealing seam, which markedly differs from the prior-art solutions. Contrary to prior-art solutions, in which two separate chamber walls are disposed on one another from the top and from the bottom, so that the circumferential seal forms the sharp-edged sealing seams described with corresponding sealing seams, an opposite overlapping of the longitudinal edges is made available according to the present invention. An air chamber is manufactured with a chamber wall preferably from a corresponding layout, which represents a flat film. This flat film of the chamber wall is now folded up until the two longitudinal edges correspondingly overlap opposite each other. An opposite overlap is defined such that the cut surface of the respective longitudinal edge points in different directions. These different directions are preferably parallel to one another and have a 180° angle in relation to one another concerning the orientation. However, offset orientations or orientations forming an angle with one another may also be provided to guarantee a correspondingly opposite overlap. It is, however, preferable if the overlap remains identical or essentially identical and constant in the opposite direction for the two longitudinal edges along the longitudinal sealing seam.

Due to the overlap in opposite directions, the longitudinal sealing seam is configured such that it now can be in contact flatly along the chamber wall. None of the longitudinal edges can project in this manner to the outside from the chamber wall, so that sharp-edged longitudinal sealing seams are completely avoided in this manner. The longitudinal sealing seam is rather provided according to the invention with a tangentially sliding transition in the circumferential direction of the chamber wall, so that no sharp-edged formation will project to the outside any more. Compared to the prior-art solutions, this causes a marked reduction or even complete elimination of an adverse mechanical effect on the skin or tissue, especially in the bend of the elbow or in the armpit of a newborn.

The circumferential direction is defined in the sense of the present invention as the direction that represents the circumference when the blood pressure cuff is placed on the arm of a newborn. In the state in which it is placed, the longitudinal sealing seam thus also extends around the arm of the newborn, around which the blood pressure cuff is placed. Additional sealing seams or other closing means are, of course, also conceivable for fully closing the air chamber. However, the lateral sections can also be provided with prior-art transverse sealing seams, because no or only very slight adverse mechanical effects can be expected in this area due to the geometric correlation with the arm and with the tissue of the newborn. It is, however, also possible to use other closing methods or even tube material explained in more detail in the further course of this application to provide a complete airtight closure of the air chamber. An air feeding device may, of course, also be provided as part of the longitudinal sealing seam or as part of the chamber wall to make it possible to guarantee a corresponding inflation of the air chamber with air. Valve devices may also be used to make it possible to provide a corresponding controllability for inflating the air chamber with air and releasing air from the air chamber.

The orientation of the longitudinal sealing seam along the circumferential direction is preferably defined as being exactly along or essentially exactly along the circumferential direction. However, the described advantage of reducing the adverse mechanical effect on the newborn is already achieved in the sense of the present invention if the longitudinal sealing seam extends along the circumferential direction with a maximum deviation of about +45°. The fact that the longitudinal sealing seam is arranged, in principle, in the circumferential direction along this with a relatively great margin of about +45° makes it already possible to achieve a corresponding reduction of the mechanical effect on the tissue of the newborn due to the opposite overlap of the longitudinal edges.

In addition to a single longitudinal sealing seam, a second longitudinal sealing seam or a third longitudinal sealing seam is, of course, also possible to close the air chamber without a hole. Thus, the air chamber may be composed of a plurality of individual sections of the chamber wall, which are composed by two or more longitudinal sealing seams, which are correspondingly oriented along the circumferential direction. This may offer advantages especially if complex forms are desired for the blood pressure cuff It is, however, preferred if the chamber wall is formed by a single chamber wall section and/or only a single longitudinal sealing seam is formed along the circumferential direction.

In addition to the advantages in the actual application when determining the blood pressure, a blood pressure cuff according to the present invention may also offer advantages in manufacture. It is thus possible to achieve a reduction in the necessary costs, which concern both the material and the effort needed for manufacture, by forming a single longitudinal sealing seam and by using one starting material for a single chamber wall. Moreover, a reduction in weld seams to a single longitudinal sealing seam due to a manufacturing method according to the present invention can lead, as will be explained later, to a further reduction in the adverse mechanical effect of the material of the chamber wall.

It may likewise be advantageous if the width of the longitudinal sealing seam in a blood pressure cuff according to the present invention corresponds or essentially corresponds to the overlapping width of the two longitudinal edges of the chamber wall. This means that the first longitudinal edge is placed over the second longitudinal edge during the manufacture, so that an overlapping width becomes established. This width of overlap, which is also called overlapping width, may be formed both continuously and variably over the course of the circumferential direction. The longitudinal sealing seam is correspondingly adapted now in terms of a longitudinal sealing seam width according to this embodiment of the present invention to the overlapping width of the two longitudinal edges. This means that the longitudinal edges are sealed up to the end of the longitudinal edge concerning the progression of the seal. In other words, no area remains open in the overlapping area of the longitudinal sealing seam in the overlapping area of the two longitudinal edges. The two longitudinal edges are rather sealed to one another completely, so that no undercuts or free spaces remain in a nonhygienic manner, in which a bacterial focus could find refuge. In addition to an improvement of hygiene due to the avoidance of such undercuts, an undesired projection and hence an increase in the risk of an adverse mechanical effect is also reduced even further due to such an embodiment.

It is likewise advantageous if the longitudinal sealing seam is located in a blood pressure cuff according to the present invention on an outer side of the chamber section especially completely or essentially completely rather than in at least some sections in relation to the orientation of the blood pressure cuff in the state in which it is placed for measurement. The advantages according to the present invention are achieved already by the fact that the longitudinal sealing seam is oriented basically along the circumferential direction. If the longitudinal sealing seam is arranged on the outer side of the chamber section according to this embodiment, this will cause that the longitudinal sealing seam will not have any contact whatsoever with the arm of the newborn in the state in which the blood pressure cuff is placed on the arm, either. Even if the blood pressure cuff slips along the arm of the newborn into the bend of the elbow or into the armpit, this orientation on the outer side of the chamber section leads to the avoidance of contacting with the sensitive tissue areas in the bend of the elbow or in the armpit at a high degree of probability. Consequently, the advantage according to the present invention, namely, the reduction in the mechanical effect on the tissue, is improved even further by this preferred arrangement on the outer side. This embodiment may lead to further advantages especially in case of blood pressure cuffs with especially small diameters, i.e., for example, for premature babies with birth weights in the range of 500 g to 2,500 g. It is, however, also conceivable that the longitudinal sealing seam is arranged on the inner side relative to the orientation of the blood pressure cuff in the state in which it is placed or that an additional longitudinal sealing seam has such an orientation. By avoiding an arrangement on the outer side, the flexibility can be increased on the outer side and reduced on the inner side of the blood pressure cuff. This is especially advantageous in terms of making the pressure distribution more uniform during the blood pressure measurement procedure.

Another advantage is that the longitudinal sealing seam has a zigzag shape in at least some sections, especially completely or essentially completely in a blood pressure cuff according to the present invention. A zigzag shape is defined in the simplest sense according to the present invention as the correlation of two straight lines, which form an angle with one another. Curved or curve-containing sections, which provide a corresponding zigzag shape, are, of course, also conceivable. However, the individual zigzag sections preferably have a straight configuration to simplify the corresponding device for forming a corresponding sealing seam. The legs of the individual zigzag shapes preferably form an angle in the range of 170° to 100° with one another, so that a correspondingly pronounced or less pronounced zigzag shape is made available. The zigzag configuration of the two longitudinal edges is based on several legs or extents having a course with at least a first extent or leg, a second extent or leg extending from the first extent at an angle relative to the first extent and a third extent or leg extending from the second extent at an angle relative to the second extent, with subsequent further extents or legs as needed). The zigzag shape leads, independently from the actual configuration with straight or curved sealing seam sections (extents), to easier inflation in the state in which it is placed.

It is thus ensured by the zigzag shape that the stability is reduced when the cuff is placed around the arm of the newborn, so that the placement can be carried out with greater ease. This may lead to great advantages especially in case of small arm diameters and correspondingly small radii of curvature for the blood pressure cuff.

It is likewise advantageous if the surface of the chamber section and/or of the handling section has a rough surface structure in a blood pressure cuff according to the present invention. The consequence of this is that contamination of such a rough surface structure, which may also be called a textile-like surface, indicates the corresponding duration of use to the user of the blood pressure cuff quasi optically. Such a surface is also more pleasant in terms of wear on the skin Since blood pressure cuffs according to the present invention are especially such embodiments, which shall be used in a single patient only, this leads to an avoidance of undesired double use. The use in a single patient may also be called a so-called "single patient use," which may, of course, also be used for several measurements over several weeks. Thus, such a blood pressure cuff may be used constantly over several weeks in a single patient, so that a continuous or semicontinuous monitoring becomes possible.

Further, it is advantageous if the handling section and/or the chamber section in a blood pressure cuff according to the present invention have a fastening surface for fastening the handling section to the chamber section on at least one side. Such fastening surfaces are formed, for example, for forming a Velcro fastener, so that corresponding hook areas correspond on the handling section to corresponding fastening surfaces of the chamber section, which have, for example, a flocking. In addition to the formation of a Velcro fastener, reversible bonded connections or even irreversible bonded connections are, of course, also conceivable for providing such a fastening functionality. Chamber sections and/or handling sections are preferably provided essentially completely with the fastening surface. The fastening functionality may be provided by a coating on the fastening surface. For example, flocking or a configuration as a so-called "nonwoven" is thus conceivable.

Another advantage is if the fastening surface in a blood pressure cuff according to the present invention covers the longitudinal sealing seam at least partially, preferably completely or essentially completely. Especially in the case of the fastening surface on the chamber section, this causes even the last remaining adverse mechanical effect to be lessened by the stiffening by means of the longitudinal sealing seam if the fastening surface entails a correspondingly mechanically reducing effect on such influencing factors. For example, a velour material may thus be used for the fastening surface, and the coverage of the longitudinal sealing seam can lead to a further increase in comfort when the blood pressure cuff is placed. The protection of the tissue of the newborn is thus improved further by this embodiment.

It is likewise advantageous if the chamber section and/or the handling section are made integrally with one another in a blood pressure cuff according to the present invention. The integral or monolithic or one-piece configuration leads to a further reduction of the costs for the material and the manufacturing effort. Thus, a single cut of a corresponding film material can make it possible in this manner to preferably provide a one-layer handling section. A needless double or double-walled configuration of the handling section is avoided in this manner. Such a layout can also be manufactured in an especially simple and cost-effective manner by a simple cutting method. Only a reduced length of longitudinal sealing seam must be subsequently prepared to make it possible to make the blood pressure cuff available in the final version.

It may, further, be advantageous if the air chamber is formed, at least in some sections, from a tube material in a blood pressure cuff according to the present invention. A tube material is defined in the sense of the present invention as a material that has a circumferential wall in a film-like manner without a sealing seam being necessary here. Such a tube material may be provided, for example, such that two longitudinal sealing seams according to the present invention are formed, so that the air chamber is closed in a completely airtight manner at the two ends of the tube by these two longitudinal sealing seams. It is, of course, also possible, in principle, to orient the air chamber in the circumferential direction in respect to the extension of the tube, so that a transverse sealing seam must be prepared in a correspondingly closing manner only at the upper and lower ends of the tube material. If corresponding geometric conditions are observed, this may lead to further advantages concerning cost reduction in the manufacture of such a blood pressure cuff.

The present invention likewise pertains to a method for manufacturing a blood pressure cuff, especially according to the present invention, having the following steps:

Formation of an overlap of two longitudinal edges of a chamber wall of a chamber section of a blood pressure cuff, formation of a longitudinal sealing seam for the airtight connection of the two longitudinal edges, and airtight closure of an air chamber of the chamber section.

Due to the configuration of a blood pressure cuff according to the present invention, a method according to the present invention offers the same advantages that were explained in detail with reference to a blood pressure cuff according to the present invention. Further steps are, of course, conceivable for making available a blood pressure cuff according to the present invention. The airtight closure of the air chamber is preferably carried out by forming additional sealing seams, especially the transverse sealing seams mentioned already at the upper and lower ends of the chamber section.

Further advantages, features and details of the present invention appear from the following description, in which exemplary embodiments of the present invention are specifically described with reference to the drawings. The features mentioned in the claims and in the description may be essential for the present invention both individually in themselves or in any combination. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
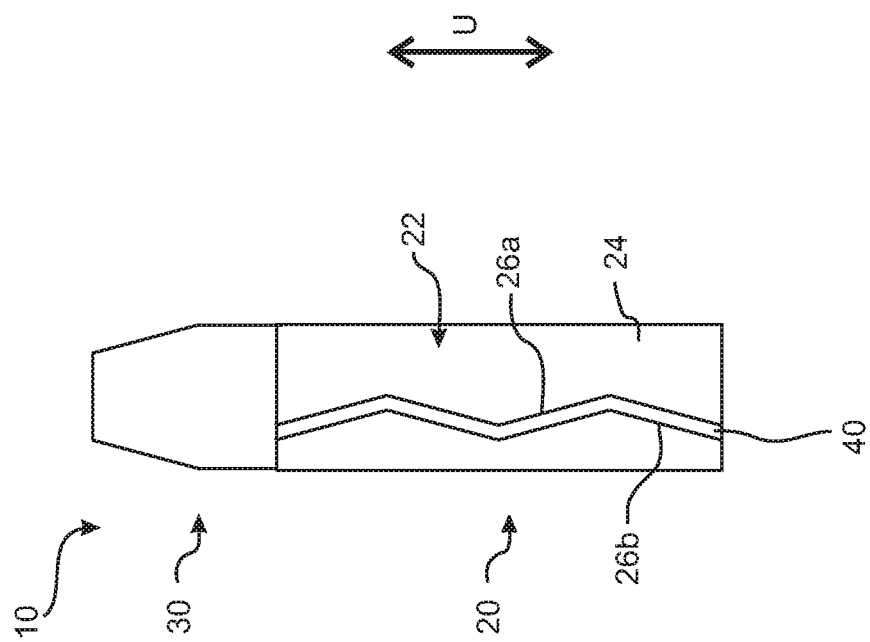
FIG. 2 is a front view the blood pressure cuff according to the layout shown in FIG. 1.
Figure 1:
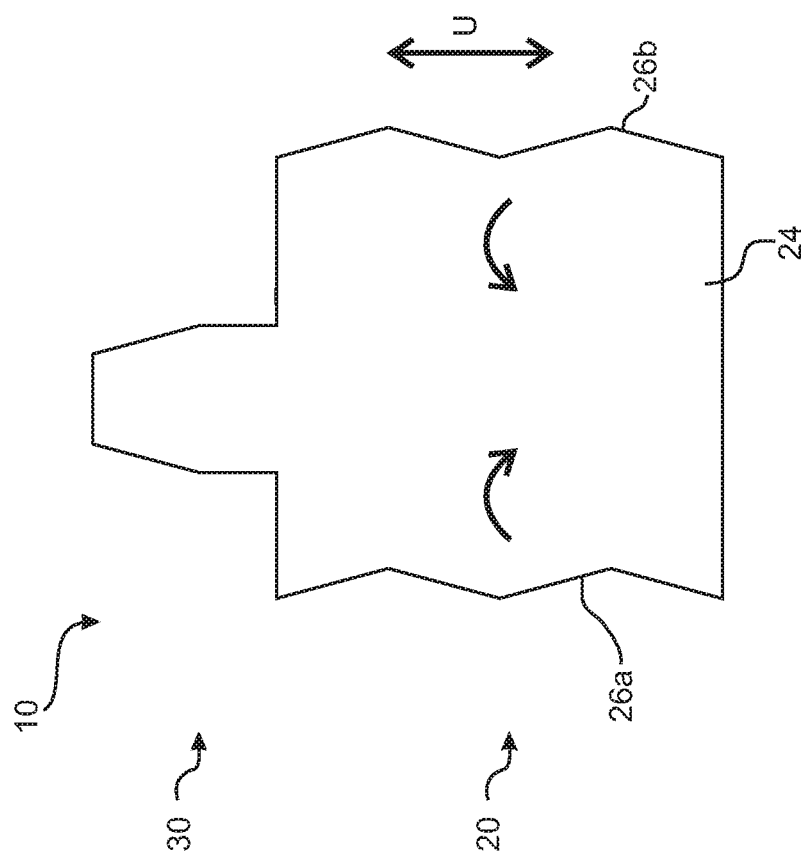
FIG. 1 is a plan view an embodiment of a layout for manufacturing a blood pressure cuff according to the present invention.
Figure 4:
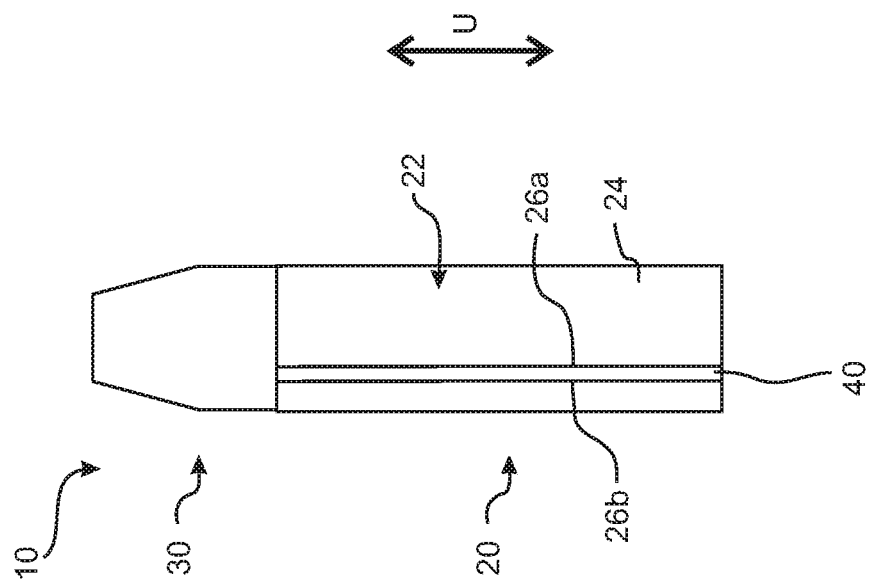
FIG. 4 is a view a blood pressure cuff manufactured from the layout according to FIG. 3.
Figure 3:
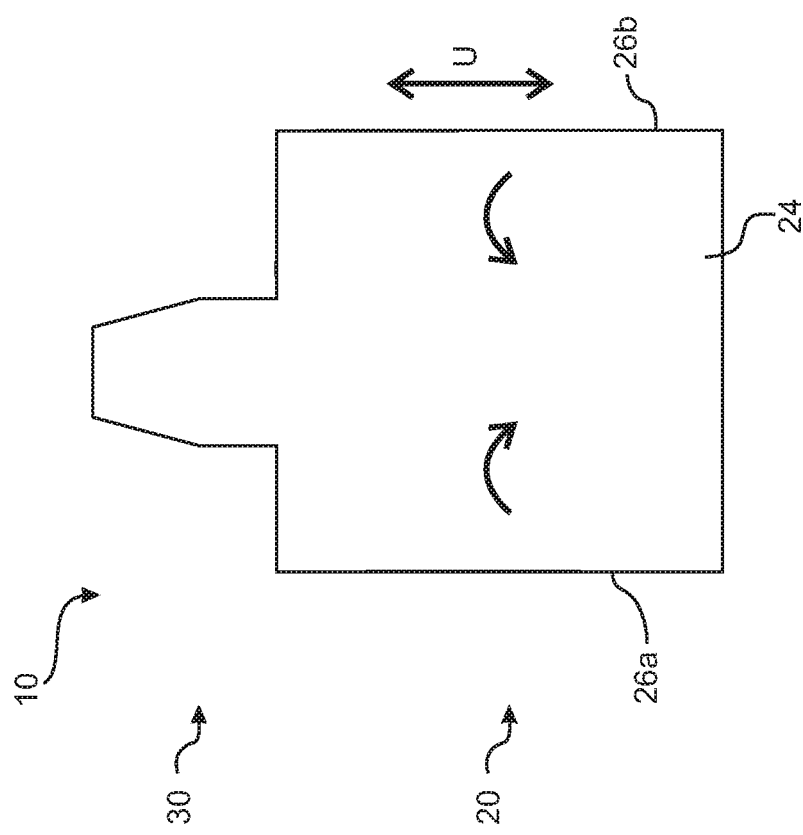
FIG. 3 is a view an embodiment of a layout for manufacturing a blood pressure cuff according to the present invention.

Referring to the drawings, FIGS. 1 and 2 as well as 3 and 4 show two different embodiments and manufacturing possibilities for a blood pressure cuff 10 according to the present invention. The simplest embodiment is shown in FIGS. 3 and 4. The two longitudinal edges 26a and 26b are folded one onto the other from a single and one-layer layout of the chamber wall 24 by folding along the directions of the arrows. An overlapping area is formed due to the overlapping, as it is already shown in FIG. 4. This overlapping area, which is formed here along the circumferential direction U essentially with a continuous width, is now sealed completely and provided with a longitudinal sealing seam 40. The airtight sealing of the air chamber 22 can subsequently be brought about at the upper and lower ends when viewed in the circumferential direction U by an additional closure, for example, by correspondingly inserting a transverse sealing seam at the upper or lower end. The handling section 30 can be formed at the upper end and a chamber section 20 in the lower area in this manner.

FIGS. 1 and 2 show essentially an identical view of a manufacturing method, but with a different geometric configuration of the longitudinal sealing seam 40. Thus, the longitudinal edges 26a and 26b of the chamber section 20 are already formed with a zigzag shape here, so that a correspondingly zigzag-shaped overlapping area is formed as well. The sealing is carried out in this zigzag-shaped overlapping area, so that a zigzag-shaped longitudinal sealing seam 40 is formed as well.

Figure 5:
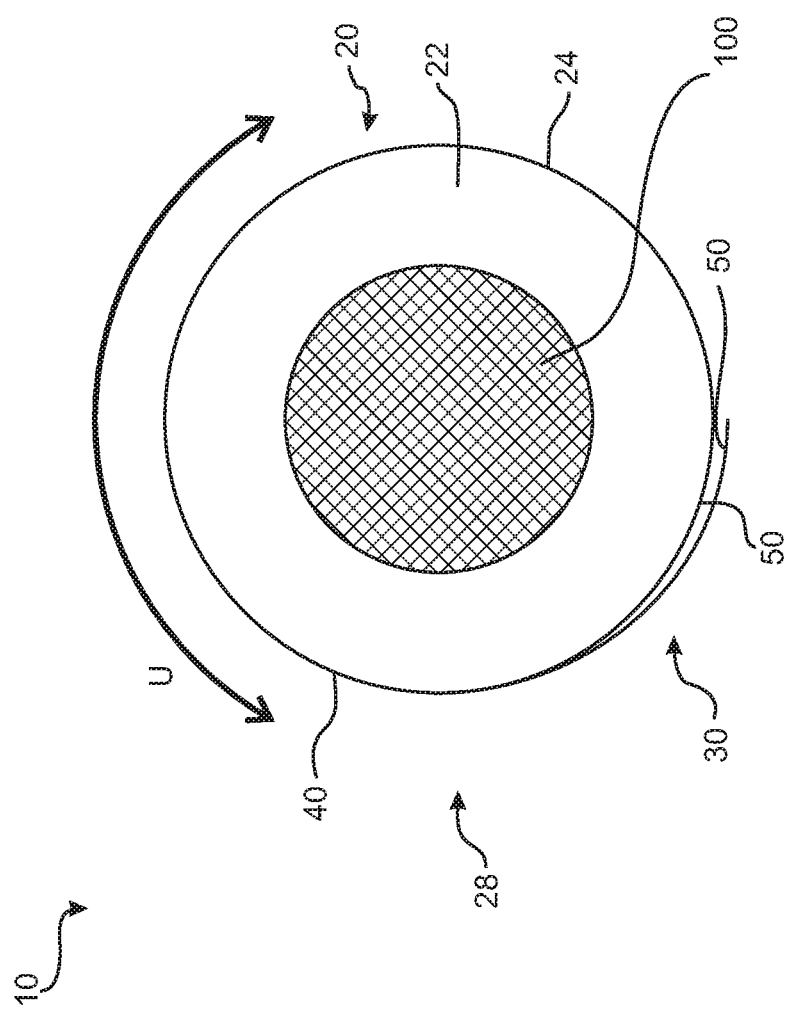
FIG. 5 is a view a blood pressure cuff according to the present invention in the state in which it is placed on the arm.

FIG. 5 shows a blood pressure cuff 10 according to the embodiments shown in FIGS. 1 and 2 as well as 3 and 4 in the state in which the blood pressure cuff is placed around the arm 100 of a newborn. The circumferential direction U is shown again here as well. In this state in which it is placed, FIG. 5 shows the inflated situation, i.e., with an increased internal pressure in the air chamber 22. The chamber wall 24 is in such an inflated situation provided with a markedly defined outer side 28, on which the longitudinal sealing seam 40 is arranged in this embodiment. It can also be easily seen here how a corresponding reversible fastening, for example, by forming a Velcro fastener, is made available by means of fastening surfaces 50 on the chamber section 20 and on the handling section 30. It can likewise be clearly seen here how the stiffness is reduced in this circumferential direction by configuring the longitudinal sealing seam 40 with a zigzag shape according to FIGS. 1 and 2, so that the blood pressure cuff 10 can be placed around the arm 100 more easily and with a reduced adverse mechanical effect.

Figure 6:
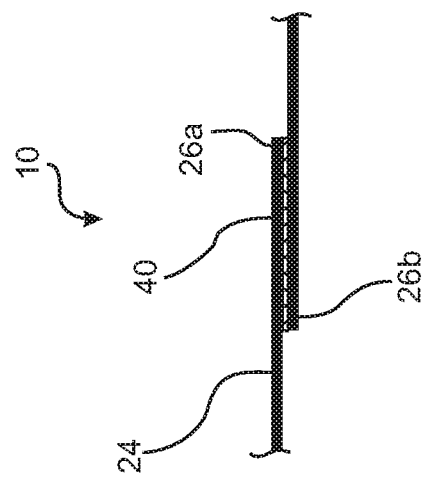
FIG. 6 is a schematic view showing a material section of the longitudinal sealing seam of an embodiment.

FIG. 6 shows a sectional view, in which the two longitudinal edges 26a and 26b can be seen from a lateral view. The overlapping of these two longitudinal edges 26a and 26b, which is directed in opposite directions, is seen here, so that free spaces and undercuts will not be formed between these two longitudinal edges 26a and 26b at all in this embodiment due to the longitudinal sealing seam 40 for the chamber wall 24 being formed completely. In addition to the reduction of the adverse mechanical effect due to the completely flat placement of such a longitudinal sealing seam 40, hygiene is improved in this manner, because no free spaces are provided any more for contamination and bacteria.

The above description of the embodiments describes the present invention exclusively within the framework of examples. Individual features of the exemplary embodiments, if technically meaningful, may, of course, be freely combined with one another without going beyond the scope of the present invention. While specific embodiments of the invention have been shown and described in detail to illustrate the application of the principles of the invention, it will be understood that the invention may be embodied otherwise without departing from such principles.

APPENDIX

List of Reference Numbers

10 Blood pressure cuff
20 Camber section
22 Air chamber
24 Chamber wall
26a Longitudinal edge
26b Longitudinal edge
28 Outer side
30 Handling section
40 Longitudinal sealing seam
50 Fastening surface
100 Arm
U Circumferential direction

What is claimed is:

1. A blood pressure cuff for determining blood pressure in newborns, the blood pressure cuff comprising:
    a chamber section with an air chamber having a chamber wall;
    a handling section for placing and fastening the chamber section around an arm of a patient;
    a longitudinal sealing seam of the chamber wall, the longitudinal sealing seam having a longitudinal sealing seam extent along a circumferential direction of the air chamber, the longitudinal sealing seam connecting two longitudinal edges of the chamber wall to one another, the two longitudinal edges overlapping each other and extending from an opposite direction with respect to each other, with the two longitudinal edges in an overlapped state, to form an airtight seal at the longitudinal sealing seam, each of the longitudinal edges having a course comprising at least a first extent, a second extent extending from the first extent at an angle relative to the first extent and a third extent extending from the second extent at an angle relative to the second extent and with two first end transverse edges overlapping each other and two second end transverse edges overlapping each other.

2. A blood pressure cuff in accordance with claim 1, wherein a width of the longitudinal sealing seam corresponds to an overlapping width of the two longitudinal edges of the chamber wall.

3. A blood pressure cuff in accordance with claim 1, wherein the longitudinal sealing seam is located in at least some sections on an outer side of the chamber section relative to a placement orientation of the blood pressure cuff.

4. A blood pressure cuff in accordance with claim 1, wherein a surface of the chamber section or of the handling section or of both the chamber section and the handling section has a rougher surface structure than other surfaces of the blood pressure cuff.

5. A blood pressure cuff in accordance with claim 1, wherein the handling section or the chamber section or both the handling section and the chamber section have a fastening surface on at least one side for fastening the handling section on the chamber section.

6. A blood pressure cuff in accordance with claim 5, wherein the fastening surface covers the longitudinal sealing seam at least partially.

7. A blood pressure cuff in accordance with claim 6, wherein the fastening surface covers the longitudinal sealing seam.

8. A blood pressure cuff in accordance with claim 1, wherein the chamber section and the handling section are formed integrally with one another.

9. A blood pressure cuff in accordance with claim 1, wherein the air chamber is made from a tube material in at least some sections.

10. A blood pressure cuff in accordance with claim 1, wherein the longitudinal sealing seam continues over the entire longitudinal sealing seam extent.

11. A blood pressure cuff in accordance with claim 1, further comprising:
a first end transverse sealing seam connecting two first end transverse edges of the chamber wall to one another with an airtight connection;
a second end transverse sealing seam connecting two second end transverse edges of the chamber wall to one another with an airtight connection, wherein the longitudinal sealing seam extent along a circumferential direction is from the first end transverse sealing seam to the second end transverse sealing seam.

12. A neonate blood pressure cuff comprising:
a film piece with two longitudinal edges that, with the two longitudinal edges in an overlapped state, extend from opposite directions and overlap as overlapping edges, each of the longitudinal edges having a course comprising at least a first extent, a second extent extending from the first extent at an angle relative to the first extent and a third extent extending from the second extent at an angle relative to the second extent and with two first end transverse edges overlapping each other and two second end transverse edges overlapping each other;
a longitudinal sealing seam connecting the overlapping edges to one another with an airtight connection;
a first end transverse sealing seam connecting the two first end transverse edges to one another with an airtight connection;
a second end transverse sealing seam connecting the two second end transverse edges to one another with an airtight connection, wherein the longitudinal sealing seam follows the course of the overlapping edges to provide a chamber wall with the longitudinal sealing seam course along a circumferential direction from the first end transverse sealing seam to the second end transverse sealing seam and cooperating with the first end transverse sealing seam and the second end transverse sealing seam to form a chamber section with an air chamber having a chamber wall; and
a handling section connected to the chamber section for handling the blood pressure cuff and placing and fastening the chamber section around the arm of a neonate.

13. A blood pressure cuff in accordance with claim 12, wherein the course of the overlapping edges, and the longitudinal sealing seam forms a zigzag configuration extending in the circumferential direction of the chamber section and the air chamber is closed by forming the transverse sealing seams at upper and lower ends of the chamber section.

14. A blood pressure cuff in accordance with claim 13, wherein the handling section or the chamber section or both the handling section and the chamber section have a fastening surface on at least one side for fastening the handling section on the chamber section.

15. A blood pressure cuff in accordance with claim 14, wherein the fastening surface covers the longitudinal sealing seam at least partially.

16. A blood pressure cuff in accordance with claim 13, wherein the chamber section and the handling section are formed integrally with one another.

17. A neonate blood pressure cuff method comprising the steps of:
providing a film piece with two longitudinal edges having a zigzag shape in at least some sections;
overlapping the two longitudinal edges, with the two longitudinal edges extending from opposite directions, in an overlapped state of the two longitudinal edges, to form a chamber wall of a chamber section of a blood pressure cuff;
forming a longitudinal sealing seam for an airtight connection of the two longitudinal edges, wherein the longitudinal sealing seam has a longitudinal sealing seam extent along a circumferential direction of the air chamber section, wherein each of the longitudinal edges has a course comprising at least a first extent, a second extent extending from the first extent at an angle relative to the first extent and a third extent extending from the second extent at an angle relative to the second extent and with two first end transverse edges overlapping each other and two second end transverse edges overlapping each other;
and closing the chamber section to provide an airtight closure of the chamber section.

18. A blood pressure cuff method in accordance with claim 17, wherein:
the air chamber is closed by forming a first transverse sealing seam at a first end of the chamber section and forming a second transverse sealing seam at a second end of the chamber section; and
the longitudinal sealing seam extent is from an upper end sealing seam to a lower end sealing seam.

19. A blood pressure cuff method in accordance with claim 17, wherein the chamber section and a handling section are formed integrally with one another.

20. A blood pressure cuff method in accordance with claim 17, wherein the longitudinal sealing seam is located in at least some sections on an outer side of the chamber section relative to a placement orientation of the blood pressure cuff when placed on a neonate.

* * * * *